United States Patent [19]

Usami et al.

[11] Patent Number: 4,908,575
[45] Date of Patent: Mar. 13, 1990

[54] CIRCUIT FOR MEASURING DIFFUSION-LIMITED CURRENT

[75] Inventors: Jun Usami, Aichi; Yuichi Sasaki, Nagoya, both of Japan

[73] Assignee: NGK Insulators, Ltd., Nagoya, Japan

[21] Appl. No.: 73,969

[22] Filed: Jul. 15, 1987

[30] Foreign Application Priority Data

Jul. 15, 1986 [JP] Japan ................................ 61-166266

[51] Int. Cl.$^4$ ............................................. G01N 27/04
[52] U.S. Cl. .................................. 324/711; 204/406; 204/425; 324/446
[58] Field of Search ...................... 324/71.1, 425, 446; 204/406, 424, 425, 432

[56] References Cited

U.S. PATENT DOCUMENTS

| 4,464,244 | 8/1984 | Uchida et al. | 204/406 X |
| 4,543,176 | 9/1985 | Harada et al. | 204/425 X |
| 4,595,485 | 6/1986 | Takahashi et al. | 204/406 |
| 4,702,816 | 10/1987 | Hashimoto et al. | 204/406 |
| 4,718,999 | 1/1988 | Suzuki et al. | 204/406 |

FOREIGN PATENT DOCUMENTS

| 3313783 | 10/1983 | Fed. Rep. of Germany . |
| 3445727 | 7/1985 | Fed. Rep. of Germany . |
| 3445754 | 8/1985 | Fed. Rep. of Germany . |
| 3445755 | 8/1985 | Fed. Rep. of Germany . |
| 3543759 | 7/1986 | Fed. Rep. of Germany . |
| 128349 | 7/1985 | Japan ................................ 324/71.1 |
| 2075197 | 11/1981 | United Kingdom . |

Primary Examiner—Reinhard J. Eisenzopf
Assistant Examiner—Robert W. Mueller
Attorney, Agent, or Firm—Arnold, White & Durkee

[57] ABSTRACT

A circuit is utilized for measuring a diffusion-limited current which flows through a diffusion-limited current element in proportion to an oxygen concentration which includes an output resistor connected in series with the element, a differential amplifier having a first input connected to a reference voltage supply source, a second input connected to ground, an output connected to the output resistor, and a feedback resistor connected between the first input of the differential amplifier and a point between the element and the output resistor, so that a bias voltage applied across the element is kept constant.

4 Claims, 2 Drawing Sheets

CIRCUIT FOR MEASURING DIFFUSION-LIMITED CURRENT

BACKGROUND OF THE INVENTION

1. Field of the Invention and Related Art Statement

The present invention relates to a circuit for measuring a diffusion-limited current for use in an oxygen concentration sensor and the like.

An oxygen sensor for measuring an oxygen concentration in a gas to be measured has been widely used. In such a sensor the atmospheric air defining a standard or reference oxygen concentration is brought to one surface of a cell body made by zirconia ceramics, the measured gas is brought to the other surface of said cell, and a given bias voltage is applied across the cell body. Then, an amount of current passing across the cell body is proportional to the oxygen concentration in the gas to be measured. Therefore, by detecting the current, it is possible to measure the oxygen concentration. As shown in FIG. 1, the current flowing across the zirconia body becomes substantially constant within a given range of the bias voltage and the current is dependent solely upon the oxygen concentration. FIG. 1 is a graph showing a variation of the current by taking, as a parameter, oxygen concentrations from 1% to 4%, while the bias voltage is applied across electrodes provided on the surfaces of the cell body. The current is increased in proportion to the bias voltage within a range from zero voltage to a given voltage. Thereafter, the current remains substantially constant even though the bias voltage is increased in a range from said given voltage to a specific voltage. This region is called the diffusion-limited current region. When the bias voltage is increased beyond the specific value, the current increases again in proportion to the applied bias voltage. This region is called the ion conduction region. That is to say, under a given bias voltage condition, the current is limited predominantly by the ion diffusion. Thus, in general, such a current is called the diffusion-limited current and the cell producing such a current is termed the diffusion-limited current element.

FIG. 2 is a circuit diagram showing a known circuit for detecting the diffusion-limited current. A diffusion-limited current element 1 constructed in the form of a tube has an inner electrode 1a connected to ground and an outer electrode 1b connected to an output resistor 2 for deriving an output signal. The output resistor 2 is connected via a current driving transistor 3 to a supply source voltage $V_s$. A base electrode of the driving transistor 3 is connected through current limiting resistor 4 and buffer amplifier 5 to a potentiometer 6 whose one end is connected to a point between a Zener diode 7 and a resistor 8 and the other end being connected to ground via a resistor 9. A series circuit of the Zener diode 7 and resistor 8 is connected across a voltage supply source $+V$ and ground. Further, a diode 10 is connected between the base and emitter of the driving transistor 3. In this known circuit, to the base of driving transistor 3 is applied a constant reference voltage produced by the Zener diode 7, so that a constant voltage is applied across the series circuit of the diffusion-limited current element 1 and output resistor 2. Therefore, across the output resistor 2 a voltage drop is produced which is proportional to the diffusion-limited current flowing through the element 1. Therefore, by monitoring the voltage drop across the output resistor 2, it is possible to measure the concentration of oxygen contained in the gas which is brought into contact with the outer surface of the element 1, while the inner surface of the element is brought into contact with the reference gas defining the reference oxygen concentration.

In the above explained circuit for measuring the diffusion-limited current, when the diffusion-limited current I flows through the element 1, the voltage applied across the element is decreased by an amount equal to I.R, wherein R is a resistance of the output resistor 2. Therefore, the bias voltage applied across the element 1 is varied as shown by an inclined line B, even if the constant bias voltage $V_B$ is applied across the series circuit of the element 1 and output resistor 2 as illustrated by a vertical line A in FIG. 1. Then, the precision of measurement is decreased and a measurable range of the oxygen concentration is limited. In order to avoid the above drawbacks, in the known circuit the voltage drop across the resistor 2 is made small. For instance, the resistance R of the output resistor 2 is chosen such that the maximum voltage drop across the output resistor does not become higher than about 0.3 V. Therefore, an amplitude of the output signal, i.e. the voltage drop across the output resistor 2 becomes extremely small and S/N of the current signal could not be made high.

SUMMARY OF THE INVENTION

The present invention has for its object to provide a novel and useful circuit for measuring the diffusion-limited current, which can remove the above mentioned drawbacks of the known circuit and can generate an output voltage having a large amplitude, while the bias voltage applied across the diffusion-limited current element can be maintained substantially constant over a wide range of the gas concentration, so that S/N of the current signal and the measurable range can be increased.

According to the invention, in a circuit for measuring a diffusion-limited current flowing through a diffusion-limited current element including an output resistor connected in series with the diffusion-limited current element for converting the diffusion-limited current into an output signal and a constant voltage source for applying a constant voltage across a series circuit of the diffusion-limited current element and output resistor, the improvement is characterized in that said constant voltage source comprises:

a first means for generating a constant reference voltage;

a second means for receiving the constant reference voltage and generating said constant voltage applied across the series circuit of the diffusion-limited current element and output resistor; and a third means for feeding back a potential at a point between the diffusion-limited current element and the output resistor to said second means such that the potential at said point is remains constant and a constant bias voltage is applied across the diffusion-limited current element.

DESCRIPTION OF THE PREFERRED EMBODIMENTS

Figure 3:
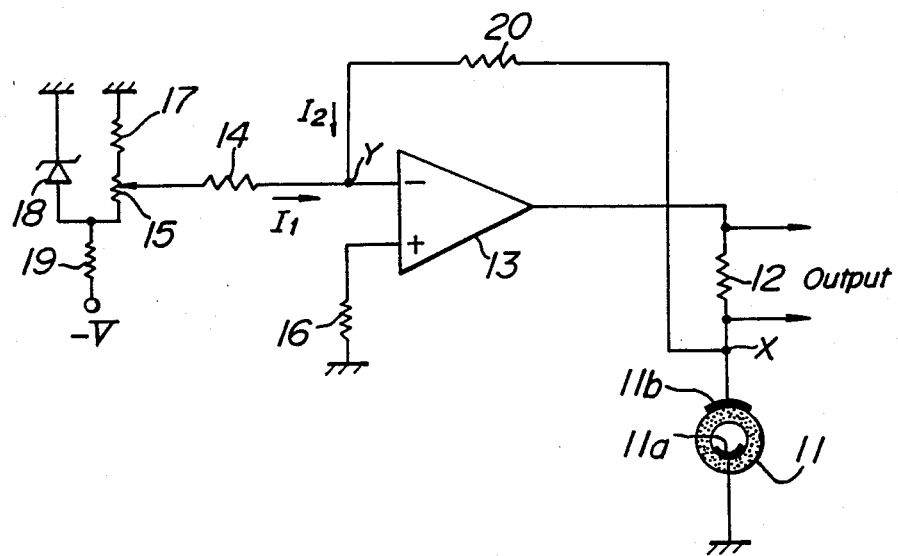
FIG. 3 is a circuit diagram depicting an embodiment of the measuring circuit according to the invention.

FIG. 3 is a circuit diagram showing a first embodiment of the diffusion-limited current measuring circuit according to the invention. In FIG. 3, a reference numeral 11 denotes a diffusion-limited current element for measuring the oxygen concentration. The element 11 is constructed in the form of a tube and made of zirconia. An inner electrode 11a of the element 11 is connected to the ground and an outer electrode 11b is connected to one end of an output resistor 12. The other end of the output resistor 12 is connected to an output of a differential amplifier 13. A negative input of the differential amplifier 13 is connected via an input resistor 14 to a potentiometer 15, and a positive input of the differential amplifier 13 is connected to the ground by means of a resistor 16. Thus, the positive input of the differential amplifier 13 is kept at zero voltage. A series circuit of the potentiometer 15 and a resistor 17 is connected in parallel with a Zener diode 18 which is connected to a voltage supply source $-V$ via a resistor 19 and to the ground. A point X between the diffusion-limited current element 11 and output resistor 12 is connected via a feedback resistor 20 to the negative input of the differential amplifier 13.

Figure 1:
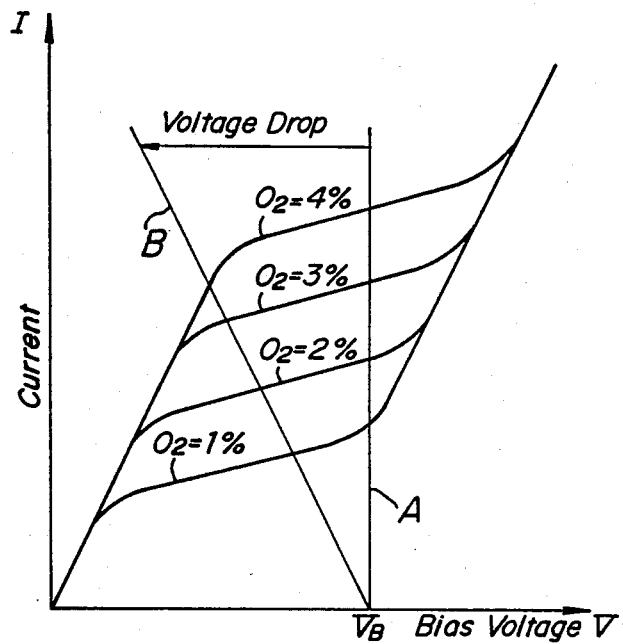
FIG. 1 is a graph showing a relationship between a bias voltage across the diffusion-limited current element and a current flowing therethrough.
Figure 2:
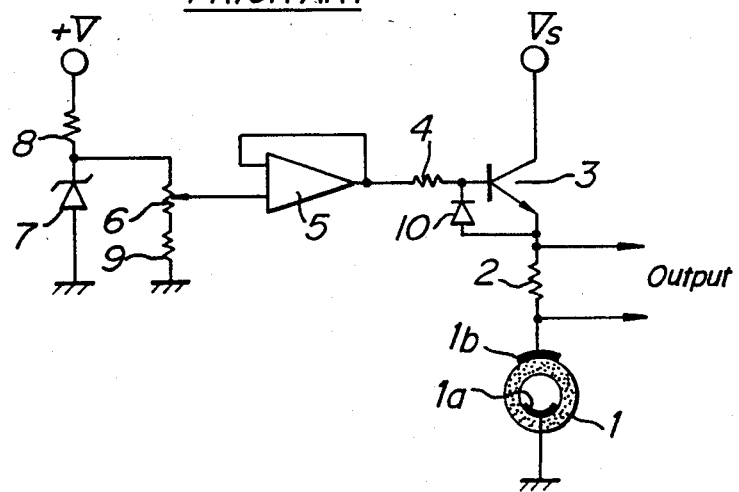
FIG. 2 is a circuit diagram illustrating a known circuit for measuring the diffusion-limited current.

In the measuring circuit shown in FIG. 3, current supplied from the output of the differential amplifier 13 is flown into the series circuit of the diffusion-limited current element 11 and output resistor 12. A diffusion-limited current passing through the element 11, in accordance with the oxygen concentration, is converted into the voltage by the output resistor 12, and the converted voltage is derived as an output signal. According to the invention, the positive input of the differential amplifier 13 is always kept at zero voltage, so that the potential at the negative input is also remains at zero voltage. Therefore, a current $I_1$ supplied from the input resistor 14 to a point Y of the negative input of the differential amplifier 13 and a current $I_2$ supplied from the feedback resistor 20 to the point Y become equal to each other. In this case, since the current $I_1$ remains constant by the function of the Zener diode 18, the other current $I_2$ is adjusted to also remain constant. The current $I_2$ is equal to a quotient obtained by dividing a voltage $V_X$ at a point X by a resistor $R_{20}$ of the feedback resistor 20 ($I_2 = V_x/R_{20}$), so that the voltage $V_x$ at the point X is always kept constant. This means that the bias voltage applied across the diffusion-limited current element 11 is remained constant even if the diffusion-limited current through the element and the voltage drop across the output resistor 12 vary. Therefore, by setting the constant bias voltage applied across the element 11 to a desired value $V_B$ shown in FIG. 1, it is possible to derive the output signal having a large amplitude so that the measuring precision can be maintained high. Further, S/N of the output signal and the measurable range of the oxygen concentration can be increased to a large extent.

Figure 4:
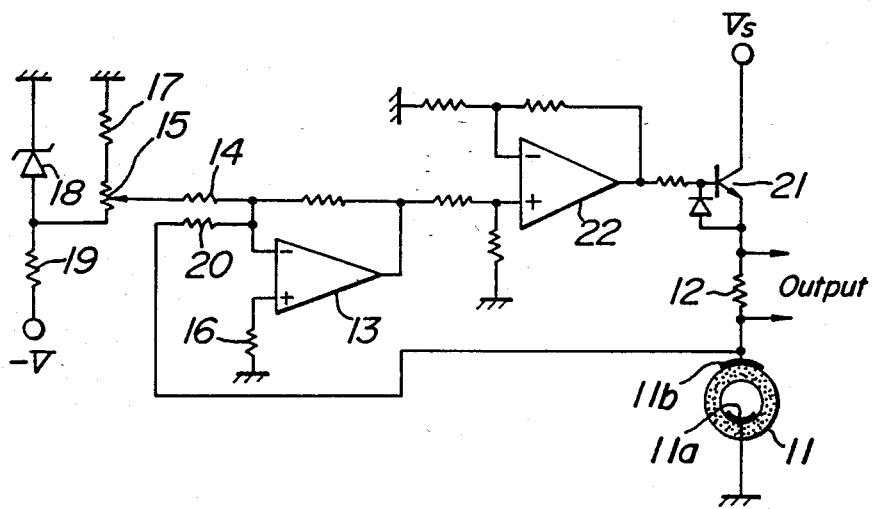
FIG. 4 is a circuit diagram showing another embodiment of the measuring circuit according to the invention.

FIG. 4 is a circuit diagram illustrating a second embodiment of the measuring circuit according to the invention. In the first embodiment shown in FIG. 3, the series circuit of the diffusion-limited current element 11 and output resistor 12 is directly connected to the output of the differential amplifier 13. In the present embodiment, a current driving transistor 21 and a buffer amplifier 22 are connected between the output resistor 12 and the output of the differential amplifier 13. Therefore, the driving transistor 21 can supply a sufficiently large amount of current to the series circuit of the diffusion-limited current element 11 and output resistor 12. The circuit of this embodiment is preferably used in such cases that a distance from the output resistor 12 for detecting the signal from the diffusion-limited current element 11 is long so that the signal might be affected by a noise from other electric circuits, and that an area of the electrode exposed to the measured gas of the diffusion-limited current element 11 is larger than an area of the electrode exposed to the standard gas. The operation of the circuit of the present embodiment is substantially similar to that of the previous embodiment and its detailed explanation is dispensed with.

As explained above, in the measuring circuit according to the invention, the bias voltage applied across the diffusion-limited current element can be kept substantially constant with the aid of the feedback means, so that the resistance of the output resistor for converting the diffusion-limited current into the output signal can be made high. Therefore, S/N of the output signal can be increased and the measurable range of the gas concentration can be widened. Thus, the oxygen concentration and the like can be detected precisely and reliably for a gas combustion-type furnace and internal engines.

What is claimed is:

1. In a circuit for measuring a gas concentration with the aid of a diffusion-limited current element having first and second electrodes, through said element, a diffusion-limited current flowing in proportion to the gas concentration including an output resistor connected in series with the diffusion-limited current element for converting the diffusion-limited current into an output signal and a bias voltage source for applying a bias voltage across a series circuit of the diffusion-limited current element and the output resistor, said bias voltage source comprising:

a reference voltage generator for generating a constant reference voltage at an output;

a differential amplifier having positive and negative inputs and an output, said output of the differential amplifier being connected to one end of said output resistor;

first conductor means connected between the other electrode of the diffusion-limited current element and the ground potential;

second conductor means connected between the positive input of the differential amplifier and the ground potential;

a first resistor connected between the output of said reference voltage generator and the negative input of the reference voltage generator; and a second resistor connected between a junction point between the other electrode of the diffusion-limited current element and the output resistor and the negative input of the differential amplifier, whereby the bias voltage applied across the diffusionlimited current element is kept constant.

2. In a circuit for measuring a gas concentration with the aid of a diffusion-limited current element through which diffusion-limited current flows in proportion to the gas concentration including an output resistor connected in series with the diffusion-limited current for converting the diffusionlimited current into an output signal and a constant voltage source for applying a constant voltage across a series circuit of the diffusion-limited current element and output resistor, wherein said constant voltage source comprises:

first means for generating a constant reference voltage including a Zener diode, a first resistor connected in parallel with the Zener diode to form a parallel circuit between the ground potential and the voltage supply source, and a second resistor coupled between the parallel circuit and a differential amplifier;

second means for receiving the constant reference voltage and generating said constant voltage applied across the series circuit of the diffusion-limited current element and output resistor; and third means for feeding back a potential at a point between the diffusion-limited current element and the output resistor to said second means such that the potential at said point remains constant and a constant bias voltage is applied across the diffusion-limited current element;

wherein said second means further comprises said differential amplifier, said differential amplifier comprising first and second inputs and an output, said first input being coupled with said first means, said second input being coupled with a constant reference potential point, and the output being coupled with said output resistor at its end which is remote from the end connected to the diffusion-limited current element, and said third means comprises a feedback resistor having one end connected to said point between the diffusion-limited current element and the output resistor and the other end connected to the first input of the differential amplifier.

3. A circuit according to claim 2, wherein said second input of the differential amplifier is connected to the ground potential by means of a resistor.

4. In a circuit for measuring a gas concentration with the aid of a diffusion-limited current element through which diffusion-limited current flows in proportion to the gas concentration including an output resistor connected in series with the diffusion-limited current for converting the diffusionlimited current into an output signal and a constant voltage source for applying a constant voltage across a series circuit of the diffusion-limited current element and output resistor, wherein said constant voltage source comprises:

first means for generating a constant reference voltage including a Zener diode, a first resistor connected in parallel with the Zener diode to form a parallel circuit between the ground potential and the voltage supply source, and a second resistor coupled between the parallel circuit and a differential amplifier;

second means for receiving the constant reference voltage and generating said constant voltage applied across the series circuit of the diffusion-limited current element and output resistor; and third means for feeding back a potential at a point between the diffusion-limited current element and the output resistor to said second means such that the potential at said point remains constant and a constant bias voltage is applied across the diffusion-limited current element;

wherein said second means comprises said differential amplifier, said differential amplifier comprises first and second inputs and an output, said first input being connected to said first means and said second input being coupled with a reference potential, a buffer amplifier having an input connected to said output of the differential amplifier and an output, and a driving transistor coupled with said buffer amplifier and connected in series with said series circuit of the diffusion-limited current element and output resistor, and said third means comprises a feedback resistor having one end connected to said point between the diffusion-limited current element and the output resistor and the other end connected to said first input of the differential amplifier.

* * * * *